United States Patent [19]
Babb et al.

[11] Patent Number: 4,717,652
[45] Date of Patent: Jan. 5, 1988

[54] COMPOSITION FOR DETECTION OF PERITONEAL INFLAMMATION OR INFECTION

[75] Inventors: James L. Babb, Libertyville; Timothy G. Bloomster, Grayslake; Jon A. Rudbach, Libertyville, all of Ill.

[73] Assignee: Abbott Laboratories, North Chicago, Ill.

[21] Appl. No.: 921,518

[22] Filed: Oct. 22, 1986

Related U.S. Application Data

[62] Division of Ser. No. 658,020, Oct. 5, 1984, Pat. No. 4,654,298.

[51] Int. Cl.$^4$ .......................... C12Q 1/00; C12Q 3/00
[52] U.S. Cl. ........................................... 435/4; 435/14; 435/15; 435/18; 435/19; 435/21; 435/23; 435/24; 435/25; 435/26; 435/28; 436/17
[58] Field of Search ................. 436/17; 435/4, 14, 15, 435/18, 19, 21, 23, 24, 25, 26, 28

[56] References Cited

U.S. PATENT DOCUMENTS 4,528,274  7/1985  Carter et al. .......................... 436/10

OTHER PUBLICATIONS

Berger et al–Chem. Abst., vol. 93 (1980), p. 65418g.
Berger et al–Chem. Abst., vol. 94 (1981), p. 43719z.
Flegler–Chem. Abst., vol. 101 (1984), pp. 226, 327c.

Primary Examiner—Sam Rosen
Attorney, Agent, or Firm—Martin L. Katz; Donald L. Corneglio

[57] ABSTRACT

Peritoneal inflammation or infection can be detected in a patient by assaying a peritoneal lavage sample from the patient for lysosomal enzymes. This is done by combining the lavage sample with a leukocyte lysing agent and a chromogenic or fluorogenic enzyme substrate specific for lysosomal enzymes. The lysosomal enzymes can then be measured, and the inflammation of infection detected, by measuring the color or fluorescence developed in the sample by action of the enzymes on the substrate.

4 Claims, No Drawings

4,717,652

COMPOSITION FOR DETECTION OF PERITONEAL INFLAMMATION OR INFECTION

This is a division, of application Ser. No. 658,020, filed Oct. 5, 1984, now U.S. Pat. No. 4,654,298.

TECHNICAL FIELD

This invention relates to a method for the rapid, early detection of peritoneal inflammation or infection in a susceptible patient. In particular, it relates to the detection of peritoneal inflammation or infection by identification of peritoneal leukocyte lysosomal enzymes in a sample of peritoneal lavage from the susceptible patient.

BACKGROUND ART

The technique of continuous ambulatory peritoneal dialysis (CAPD) for patients with chronic kidney disease or kidney failure is now well known. In this technique, metabolic waste products and excess electrolytes and other materials are washed from the body on a continuous basis by fluid infused into the peritoneal cavity, using the peritoneal membrane as a dialyzing membrane. The fluid for dialysis is introduced into the peritoneal cavity by a transabdominal connection. By virtue of the introduction of this artificial connection to the peritoneal cavity, these patients are exposed to an increased risk of peritoneal inflammation or peritoneal infection, commonly referred to as peritonitis.

In addition, large numbers of patients present themselves to emergency rooms complaining of abdominal distress and demonstrating other evidence of infection. In these patients, too, the differential diagnosis of peritonitis from other abdominal pathology is of timely importance.

Acute inflammation and infection has been known to be associated with increased numbers of granulocytic leukocytes in the peritoneal fluid. A routine laboratory procedure for detecting increased levels of peritoneal leukocytes uses microscopy techniques which require expensive instrumentation and technical expertise. Similarly, the presence of an infection has been routinely detected by microbial culturing, which commonly requires a 24–48 hour incubation period. During this incubation time, serious complications or extensive progression of the disease state can occur, further exacerbating the patient's condition or forcing the physician to treat the patient on the basis of incomplete information. It would therefore be desirable to have a rapid, inexpensive test for peritoneal inflammation and infection which requires no instrumentation, which can be performed by untrained personnel, and which could, if desired, be performed at the bedside or in the home, so that CAPD patients could be routinely monitored for complications.

DISCLOSURE OF THE INVENTION

This invention is a method for detection of an acute inflammatory response in the peritoneal cavity that may indicate an infection. A positive reaction in the test of this invention alerts the patient that help is necessary, or the physician that therapy is indicated. This invention is based on the principles that increased levels of granulocytic leukocytes are pathognomonic indicators of infection, and that these granulocytes contain lysosomal enzymes. Thus, detection and quantification of this lysosomal enzyme activity in peritoneal dialysate fluid or other peritoneal lavage fluid can be a sensitive, rapid and relatively specific method for the early detection of an infection or peritonitis. The assay of this invention requires no instrumentation, takes less than 15 minutes, and is sensitive and specific. It can be performed by dialysis patients in the home on a routine basis. In the method of this invention, a peritoneal lavage sample from a patient is combined with a leukocyte lysing agent and a chromogenic or fluorogenic enzyme substrate specific for lysosomal enzymes. The sample then changes to a varying degree depending upon the level of lysosomal enzyme activity in the lavage sample. The sample can then be read by untrained personnel by a simple comparison with a standardized reactivity scale. At the same time, the practice of this invention by automated or instrumental methods is also contemplated. As might be expected, spectrophotometric analysis of the sample color can permit more precise measurements of results, and automation of sample preparation and measurement can permit more efficient processing of large numbers of samples.

INDUSTRIAL APPLICABILITY

In its simplest form, the method of this invention requires only three components, a peritoneal lavage sample, a leukocyte lysing agent and an enzyme substrate. The peritoneal lavage sample can be obtained by any convenient means. If the patient is a CAPD patient, a sample of dialysate fluid can be taken as the spent fluid is removed from the peritoneal cavity. In other patients, the peritoneal washing or lavage can be performed by conventional transabdominal techniques readily familiar to the physician. In the latter case, because a smaller volume of fluid is usually used, dilution of the sample or use of a smaller sample is appropriate if the reaction is to be read from the same color scale used for CAPD patients, because of the difference in dilution.

In order to detect the leukocyte lysosomal enzymes, the enzymes must be released from the leukocytes by lysis. A very wide variety of materials can be used to lyse the leukocytes, and the selection of the lysing agent is not particularly critical. For example, a detergent which does not interfere with the enzymatic or other reactions and which does not interfere with reading of the results can be used. A preferred lysing agent for this purpose is saponin.

By "chromogenic enzyme substrate" and "fluorogenic enzyme substrate" is meant respectively those compounds which directly produce a colored or fluorescent product when acted upon by the lysosomal enzymes. It also includes compounds which, when acted upon by the enzyme, produce a product which can further react with another compound to produce the desired color or fluorescence. Thus, although a two-component test composition can easily be used, multiple component test compositions are also contemplated. If a fluorogenic substrate system is employed, a fluorescence-stimulating light source, such as a blacklight, can be used in reading the sample, or fluoresence spectrometry apparatus can be used if more precise readings are necessary.

A variety of chromogenic and fluorogenic substrates for the lysosomal enzymes can be used. Leukocyte lysosomes contain a variety of enzymes, including peroxidase, sulfatase, acid phosphatase, alkaline phosphatase, $\beta$-glucuronidase, acid $\beta$-glycerophosphatase, ribonuclease, cathepsin, lysozyme, and phagocytin. Substrates for any of these can be used. The substrate is preferably selected to produce a color change or fluoresence which is detectable to the naked eye, and which provides a sufficient gradation of reaction depending upon the concentration of lysosomal enzymes in the lavage sample. In this manner, the use of spectrophotometric methods or skilled personnel to read the sample can be avoided. A preferred enzyme substrate for this purpose is O-phenylenediamine, but other substrates, such as 5-thio-2-nitrobenzoic acid, a mixture of 3-methyl-2-benzothiazolinone hydrozone and 3-(dimethylamino) benzoic acid, 4-chloro-1-napthol, napthol blue, nitrophenyl guanidinobenzoate, 2,3-azino-di-(3-ethylbenzothiazoline sulfone-6) diammonium salt, 5-aminosalicylic acid, and fluorescein acetate or other fluorescein esters could be used.

In use, the enzyme detecting composition, containing the lysing agent and a chromogenic or fluorogenic substrate, is added to an aliquot of peritoneal lavage in any convenient manner. For example, the enzyme detecting composition can be a liquid or powder which is simply added to the lavage sample and mixed. Or the composition can be impregnated in an absorbent material which is then dipped in the lavage sample, as is done with common urinalysis tests. In yet another embodiment, the inner surface of a suitable reaction container can be coated with the detecting composition. When an aliquot of lavage fluid is added to the container, the test reactions occur. The mixture is preferably allowed to react for ten minutes at room temperature.

When the lavage sample has been lysed and reacted, it can be read immediately. The amount of color change or fluorescence observed is directly proportional to the number of peritoneal leukocytes, over the diagnostic range. In general, leukocyte counts of $10^4$ to $10^5$ per ml of lavage sample are considered indicative of peritonitis or peritoneal inflammation. Specific application of this technique and these principles is further illustrated by the following example.

EXAMPLE

Peritoneal inflammation was induced in mice by intraperitoneal injection of sterile thioglycollate broth. Four days later, peritoneal granulocytic leukocytes were harvested from the same mice by lavage with buffered normal saline. The leukocytes were counted using a Coulter TM cell counter and then diluted to known concentrations. One milliliter aliquots of each leukocyte dilution were tested by mixing with 1 ml of a test composition containing 0.015% hydrogen peroxide, 200 ug/ml saponin, and 0.4 mg/ml O-phenylenediamine, in 0.15 M citrate-phosphate buffer at pH 5.5.

The lavage dilution/test solution mixtures were allowed to react for 10 minutes at 25° C. The reactions were stopped with 1.0 ml. $H_2SO_4$ and absorbance at 490 nm (yellow-orange) was read quantitatively. Results were as follows:

| Peritoneal cells/ml. | $A_{490}$ |
|---|---|
| $1 \times 10^3$ | 0.009 |
| $5 \times 10^3$ | 0.058 |
| $1 \times 10^4$ | 0.131 |
| $5 \times 10^4$ | 0.930 |
| $1 \times 10^5$ | 1.939 |
| $3 \times 10^5$ | 2.000 |

What is claimed is:

1. A composition for the detection of leukocytes in peritoneal lavage samples consisting essentially of a leukocyte lysing agent and a chromogenic or fluorogenic enzyme substrate specific for detecting leukocyte lysosomal enzymes selected from the group consisting of peroxidase, sulfatase, acid phosphatase, alkaline phosphatase, $\beta$-glucuronidase, acid $\beta$-glycerophosphatase, ribonuclease, cathepsin, lysozyme and phagocytin.

2. A composition according to claim 1 wherein the leukocyte lysing agent is saponin.

3. A composition according to claim 2 wherein the substrate is a member selected from the group consisting of O-phenylenediamine, a mixture of 3-methyl-2-benzothiazolinone hydrozone and 3-(dimethylamino) benzoic acid, 4-chloro-1-napthol, 2,3- azino-di-(3-ethylbenzothiazoline sulfone-6) diammonium salt, and 5-aminosalicylic acid.

4. A composition according to claim 3 wherein the substrate is O-phenylenediamine.

* * * * *